United States Patent
Reichwein et al.

(10) Patent No.: US 10,093,612 B2
(45) Date of Patent: *Oct. 9, 2018

(54) PROCESS TO PREPARE PHENOLIC ETHYLENEDIAMINE DIACETIC ACID COMPOUNDS

(71) Applicant: Akzo Nobel Chemicals International B.V., Arnhem (NL)

(72) Inventors: Adrianus Maria Reichwein, Velp (NL); Hubertus Johannes Jongen, Gendringen (NL); Marjolein Groote, Deventer (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/736,367

(22) PCT Filed: Jun. 23, 2016

(86) PCT No.: PCT/EP2016/064499
§ 371 (c)(1),
(2) Date: Dec. 14, 2017

(87) PCT Pub. No.: WO2016/207165
PCT Pub. Date: Dec. 29, 2016

(65) Prior Publication Data
US 2018/0170856 A1    Jun. 21, 2018

(30) Foreign Application Priority Data
Jun. 25, 2015 (EP) .................................... 15173799

(51) Int. Cl.
*C07C 229/00* (2006.01)
*C07C 227/20* (2006.01)

(52) U.S. Cl.
CPC .................................. *C07C 227/20* (2013.01)

(58) Field of Classification Search
CPC ............................ C07C 227/20; C07C 233/12
See application file for complete search history.

(56) References Cited

U.S. PATENT DOCUMENTS

| 2,967,196 A * | 1/1961 | Kroll | C05D 9/02 534/10 |
| 3,632,637 A | 1/1972 | Martell | |
| 4,338,460 A * | 7/1982 | Gaudette | C07F 15/00 544/335 |
| 4,482,626 A | 11/1984 | Twist et al. | |
| 5,342,604 A | 8/1994 | Wilson et al. | |
| 5,776,894 A | 7/1998 | Albert et al. | |
| 6,242,492 B1 | 6/2001 | Bergeron, Jr. | |
| 8,629,293 B2 | 1/2014 | Olszewski et al. | |
| 2001/0039295 A1 | 11/2001 | Bergeron, Jr. | |
| 2004/0115572 A1 | 6/2004 | Tsukada et al. | |
| 2004/0121273 A1 | 6/2004 | Nakagawa et al. | |
| 2006/0068341 A1 | 3/2006 | Inoue | |
| 2007/0099132 A1 | 5/2007 | Nakagawa et al. | |
| 2007/0202276 A1 | 8/2007 | Arai et al. | |
| 2007/0202277 A1 | 8/2007 | Arai et al. | |
| 2007/0203024 A1 | 8/2007 | Takehara et al. | |
| 2008/0241732 A1 | 10/2008 | Hosokawa et al. | |
| 2008/0248951 A1 | 10/2008 | Yoshitani et al. | |
| 2010/0168469 A1 | 7/2010 | Nawrocki et al. | |
| 2014/0292940 A1 | 10/2014 | Cordwell et al. | |

FOREIGN PATENT DOCUMENTS

| WO | 01/46114 A1 | 6/2001 |
| WO | 2016/207266 A1 | 12/2016 |

OTHER PUBLICATIONS

Kean et al., "Iron chelating agents and their effects on the growth of *Pseudokirchneriella subcapitata, Chlorella vulgaris, Phaeodactylum tricornutum* and *Spirulina platensis* in comparison to Fe-EDTA," Journal of Algal Biomass Utilzation, 2015, 6 (1), pp. 56-73, Retrieved from the Internet: URL:http://jalgalbiomass.com/paper7vol6no1.pdf retrieved on Oct. 16, 2015, XP055221657.

Martell et al. "Synthesis of N,N'-di(2-hydroxybenzyl)ethylenediamine-N,N'-diacetic acid (HBED) and derivatives," Canadian Journal of Chemistry, vol. 64, No. 3, Mar. 1, 1986, pp. 449-456, CA ISSN: 0008-4042, DOI: 10.1139/v86-070, XP055221199.

J.G. Wilson, "Phenolic Analogues of Amino Carboxylic Acid Ligands for 99mTc. II* Synthesis and Characterization of N,N'-Ethylenebis[N-(o-hydroxybenzyl)-glycines] (ehbg)," *Aust. J. Chem.*, 1988, 41, pp. 173-182.

Chaney, "Plants Can Utilize Iron From Fe-N,N'-Di-(2-Hydroxybenzoyl)-Ethylenediamine-N,N'-Diacetic Acid, A Ferric Chelate With 106 Greater Formation Constant Than Fe-EDDHA," Journal of Plant Nutrition, 11(6-11), (1988). p. 1033-1051.

European Search Report issued in the counterpart European Application No. 15173799.6 dated Oct. 28, 2015.

Notification of Transmittal of the International Search Report and the Written Opinion of the International Searching Authority, or the Declaration from the International Bureau of WIPO for International Application No. PCT/EP2016/064499 dated Sep. 5, 2016.

* cited by examiner

*Primary Examiner* — Yevgeny Valenrod
*Assistant Examiner* — Blaine G Doletski
(74) *Attorney, Agent, or Firm* — Sandra B. Weiss

(57) ABSTRACT

The present invention relates to a process to prepare N,N'-di(2-hydroxybenzyl) ethylenediamine-N,N'-diacetic acid and salts thereof comprising a reaction between formaldehyde, ethylenediamine diacetic acid or a salt thereof and phenol at a pH of between 3 and 7 and a temperature below 60° C. wherein the reaction mixture contains 0.2 to 1.1 molar equivalents of alkali metalions on the molar amount of EDDA.

14 Claims, No Drawings

PROCESS TO PREPARE PHENOLIC ETHYLENEDIAMINE DIACETIC ACID COMPOUNDS

This application is a national stage filing under 35 U.S.C. § 371 of PCT/EP2016/064499, filed Jun. 23, 2016, which claims priority to European Patent Application No. 15173799.6, filed Jun. 25, 2015, the contents of each of which are each incorporated herein by reference in their entirety.

The present invention relates to a process to prepare phenolic ethylenediamine diacetic acid compounds and to phenolic ethylenediamine diacetic acid compounds obtainable with the process.

Phenolic ethylenediamine diacetic acid compounds are known in the art. An example of a phenolic ethylenediamine diacetic acid compound is N,N'-di(2-hydroxybenzyl)ethylenediamine-N,N'-diacetic acid, often abbreviated as HBED, though more specifically this molecule is o,o-HBED. The isomers o,p- and p,p-HBED may also be formed in production processes, though in significantly smaller amounts. Preparation methods for this molecule are described in several documents such as in WO 2009/037235 and U.S. Pat. No. 3,632,637.

The process of WO 2009/037235 involves a reductive amination of glyoxylic acid with a salan compound that is made by reacting ethylenediamine with salicylaldehyde to give HBED isolated as a dry HCl solid, which is later converted to a high pH sodium salt solution by adding sufficient NaOH. This reaction requires quite a number of steps, however, many of them of considerable complexity, and a number attended with high costs. These steps are, among others, filtering off the hydrogenation catalyst, working with H2, which requires safety measures, working under increased pressure, and using an excess of glyoxylic acid and amine proton acceptor, both of which need to be recycled before the formed HBED can be isolated in a crystalline form. Moreover, to prepare the iron chelate of HBED the crystals would need to be dissolved again before they can be contacted with iron cations and next be dried again in the iron chelated form.

The process of U.S. Pat. No. 3,632,637 involves reacting ethylenediamine diacetic acid with o-acetoxybenzyl halogenide, such as bromide or chloride.

In J. G. Wilson, "phenolic analogues of aminocarboxylic acid ligands for $^{99m}$Tc. II* Synthesis and characterization of N,N'-ethylenebis[N-(o-hydroxybenzyl glycines)] ehbg", *Aust J Chem* 1988, 41, 173-182, it is described that the above process of U.S. Pat. No. 3,632,637 is undesirable as it is marred by the formation of resinous polymeric by-products, creating a search for new preparation processes. In this same document reference is made to U.S. Pat. No. 2,967,196 as giving further preparation methods for making phenolic ethylenediamine diacetic acids.

U.S. Pat. No. 2,967,196 discloses a reaction wherein formaldehyde is added to an alkaline solution of ethylenediamine diacetic acid in methanol to which a para-substituted phenol such as p-cresol, p-phenolsulfonic acid or p-hydroxybenzoic acid is added. This is disclosed to be done to avoid a reaction of ethylenediamine diacetic acid with an o-chloromethyl derivative, which is said to be the only way to ensure the hydroxyl group ending up ortho to the ethylenediamine part of the molecule. The reaction conditions in this document involve reflux conditions, i.e. relatively high temperatures, and the reaction is preferably performed at an alkaline pH of between 8 and 10.

It is also confirmed in the above publication of J. G. Wilson that the reaction disclosed in U.S. Pat. No. 2,967,196 is not successful for unsubstituted phenols for the same ortho, para-position reason as referred to in US '196.

However, there is a need in the art to provide a process to make HBED and derivatives thereof wherein ethylenediamine diacetic acid can be reacted with formaldehyde and phenol.

The present invention now provides a process to prepare N,N'-di(2-hydroxybenzyl) ethylenediamine-N,N'-diacetic acid and salts thereof (HBED) comprising a reaction between formaldehyde, ethylenediamine diacetic acid or a salt thereof (EDDA) and phenol at a pH of between 3 and 7 and a temperature below 60° C. wherein the reaction mixture contains 0.2 to 1.1 molar equivalents of alkali metal ions on the basis of the molar amount of EDDA.

Working within the scope of the process of the present invention it has been found possible to make HBED with a good selectivity for the ortho (to hydroxyl) position and a high yield of product in a limited number of steps, using cheap materials, wherein the reaction steps are easy to control because no highly exothermic steps are involved, no high pressure needs to be applied and no hazardous materials are used, wherein pH control is relatively straightforward, and wherein the reaction mixture is also easy to handle throughout the reaction, as it is homogeneous.

It may be noted that U.S. Pat. No. 4,338,460 discloses a process for preparing phenolic propylenediamine diacetic acid compounds and that in this document an acidic pH of 2 to 6 is disclosed to be suitable for the production of di-ortho hydroxybenzyl propylenediamine diacetic acid products. However, in the examples of this same document it is demonstrated that the results obtained for propylenediamine diacetic acid could not be repeated for ethylenediamine diacetic acid products. In Example 12 where ethylene equivalents were used, a ring closure was found to take place when reacting ethylenediamine N,N' diacetic acid, formaldehyde and phenol in a water/methanol solution.

Moreover, the process of the present invention does not work properly for propylenediamine diacetic acid. Accordingly, one must conclude that reactions of ethylenediamine acetic acid with phenolic compounds and propylenediamine acetic acids with the same phenolic compounds are so essentially different that it will not be possible to predict reaction conditions for preparing HBED on the basis of what has been found in producing phenolic propylenediamine diacetic acid compounds. Furthermore, the fact that in Example 12 of U.S. Pat. No. 4,338,460 no reaction to form HBED takes place is thought, without Applicant wishing to be bound to any theory, to be due to the fact that the reaction mixture contains no alkali metal ions, which results in the reactants being relatively insoluble in the employed solvent mixture.

The present invention also provides the products obtainable by the present invention. It was found that as they were obtained by a different process, these products are different in the sense that they have another isomers distribution, contain low amounts of by-products and are an alkali metal-functional salt of HBED, containing about 0.2-1.1 molar equivalents of alkali metal per mole of HBED, in either dissolved or dry form. Additionally, the products of the process of the invention were found easy to dry. The products of the present invention, though different from those obtained in WO 2009/037235, can equally be used in many applications, such as water softening, pulp and paper production, bleaching, detergents. More preferably, they can be used for bleaching (pulp, textiles, detergents) or in micronutrient formulations. Most preferably, they are used in micronutrient formulations.

In the process of the present invention the three reactants can be added together using different orders of steps. As the phenol reactant is used as a liquid—and in many embodiments is used in an excess amount—it is possible to either make a premix of the EDDA and the phenol and next add this mixture to the formaldehyde or vice versa, or to make a premix of the phenol and formaldehyde and add this premix to the EDDA or vice versa, and then perform the reaction under the above pH, alkali metal load, and temperature conditions. Another even more preferred way of performing the process is first making an adduct of the EDDA and formaldehyde and next reacting this adduct with the phenol under the mentioned pH, alkali metal load, and temperature conditions. This latter embodiment has as an advantage that only liquids need to be reacted with one another, which provides for easier dosing to a reactor, for example by simple pumping of the components.

Hence, the invention also covers a process to prepare N,N'-di(2-hydroxybenzyl) ethylenediamine-N,N'-diacetic acid and salts thereof (HBED) comprising a first step wherein a reaction is performed between formaldehyde and ethylenediamine diacetic acid or a salt thereof to give an adduct, and a second step wherein the adduct of formaldehyde and ethylenediamine diacetic acid or a salt thereof is reacted with phenol while ensuring that the pH is between 3 and 7 and the temperature is below 60° C.; or such a process comprising a first step of preparing a mixture comprising phenol and ethylenediamine diacetic acid or a salt thereof, and a second step of reacting the EDDA and phenol in this mixture with formaldehyde at a pH of between 3 and 7 and a temperature of below 60° C.; or such a process comprising a first step of preparing a mixture comprising phenol and formaldehyde and a second step of reacting the phenol and formaldehyde in this mixture with ethylenediamine diacetic acid or a salt thereof at a pH of between 3 and 7 and a temperature of below 60° C., wherein in all the above embodiments of the process the reaction of the 3 components EDDA, phenol and formaldehyde is performed in a mixture that contains 0.2 to 1.1 molar equivalents of alkali metal ions on the basis of the molar amount of EDDA. The process wherein first EDDA and formaldehyde are mixed, next the pH is ensured to be between 3 and 7 and subsequently the reaction with phenol is allowed to take place is preferred, as this reaction proceeds through to a clear solution. Even more preferred is EDDA being transferred to the monoalkali metal salt by addition of 1 molar equivalent of alkali metal hydroxide and mixed with 2 moles of formaldehyde and next reacted with phenol. By transferring the EDDA to the monoalkali metal salt it is moreover ensured that the reaction pH is between 3 and 7.

The pH during the process is between 3 and 7, and preferably between 4 and 7; it was even found to be more preferable to maintain the pH at a value of at least 5 for good yield and selectivity. In the process of the present invention a pH below 3 was found to be detrimental.

Logically during the process water needs to be present as a solvent or co-solvent to be able to determine a pH. Preferably, the EDDA reactant is added as a solution in water, but water can equally well be present with the formaldehyde reactant or be added separately to the reaction mixture.

The alkali metal ions in embodiments are added to the reaction mixture by the addition of an alkali metal hydroxide or by adding the EDDA component as an ethylenediamine diacetate alkali metal salt or as an aqueous solution containing alkali metal ions in the right amount. When the process of the present invention proceeds by premixing 2 of the 3 components, followed by a step in which the $3^{rd}$ component is added, the alkali metal in principle only needs to be present in the reaction mixture when the $3^{rd}$ component is present and the reaction to give HBED begins; however, the alkali metal ions may be added to the earlier mixture as well. In most instances the pH is adjusted to a value of between 3 and 7 by the addition of an alkali metal hydroxide in an amount of between 0.2 and 1.1 molar equivalents on the basis of the molar amount of ethylenediamine diacetic acid or—which is effectively the same—by adding the EDDA component as an ethylenediamine diacetate salt or aqueous solution containing 0.2 to 1.1 equivalents of an alkali metal countercation. More preferably, the alkali metal is present in 0.8-1.0 molar equivalent on EDDA moles, even more preferably 0.85-0.98 molar equivalent. In a preferred embodiment the process of the present invention contains a next step wherein the product obtained is converted to the acid, another salt or metal complex. As the product of the process initially will be an alkali metal salt of HBED having about 0.2 to 1.1 alkali metal ions per HBED molecule, or a solution thereof, converting to another salt also covers a step of adding more base, such as alkali metal hydroxide, and converting the HBED salt to one containing more than about 1.1 equivalents of alkali metal countercations, or adding an acid and replacing alkali metal cations with protons. Most preferably, in a next step the prepared HBED is contacted with a multivalent metal cation, such as an iron cation, to form an—iron—chelate complex. All the above conversions are within the skills of someone skilled in the art.

In another preferred embodiment, the process contains an additional step of removing unreacted starting materials and/or by-products, a drying step, or both. This step and the above step of converting the product to an acid, salt or complex can be performed in any order.

In one embodiment, the reaction mixture can be suitably processed further by a step in which organic compounds are removed or recycled, such as an excess of phenol or formaldehyde that is used. A preferred way of removing or recycling these organic compounds is performing an extraction step with or without recycling the organic fraction back into the process. In the extraction the HBED product for the major part will be collected in the aqueous phase.

As indicated, the HBED product or derivative, such as the metal complex made from the HBED product, in some embodiments can be dried. The drying step can be performed by any drying method that a skilled person is aware of, such as drum drying, solvent evaporation, crystallization, spray drying, and in a preferred embodiment is a spray drying step.

Spray drying is preferably done in a spray drying apparatus to which the—in most instances aqueous—solution or slurry and the air are passed concurrently or countercurrently, with more preferably a temperature gradient between the aqueous solution and the incoming air in the range from 70 to 350° C., by atomizing the aqueous solution into fine liquid droplets.

The atomizing can be done by feeding an aqueous solution onto one or more disks which rotate, preferably at a peripheral speed of >=100 m/s, or by compressing it by means of a pump to a pressure of, in one embodiment, >=20 bar absolute, preferably 40 to 60 bar and, at this pressure, feeding it into the drying apparatus via one or more jets. If nozzles are used, they are preferably a few mm in size, even more preferably between 2 and 3 mm.

In a preferred embodiment, the atomizing occurs with addition of seeds, such as a crystalline fine dust, in the aqueous solution. The seeds in one embodiment have an upper limit for an average particle diameter lower by at least a factor of 2 than the lower limit of an average particle diameter of the powder obtained by the spray drying process. Preferably, the fraction of the seeds is from 0.1 to 50% by weight, preferably 0.1 to 20% by weight, based on the weight of the powder obtained by the process.

Another advantage of the present invention is that when a drying step is added, such as in preferred embodiments a spray drying step, the process leads to solid materials with improved properties, like improved storage and handling properties, wherein the drying step itself also proceeds without any problems such as dusting, caking, uneven particle sizes, plugging of the spray nozzle.

In further preferred embodiments the temperature during the process is between 0 and 60° C., preferably between 20 and 50° C., even more preferably between 30 and 50° C.

In yet other preferred embodiments of the process of the present invention the molar ratio of phenol:ethylenediamine diacetic acid (or a salt thereof) is higher than 8:1, more preferably up to 20:1; most preferably it is between 10:1 and 14:1. It is also preferred to perform the reaction in phenol as a solvent, suitably in the substantial or full absence of other solvents than water. This makes it possible to avoid contamination with other compounds. The unreacted phenol can be recycled without any problems, so in a more preferred embodiment phenol is used as a (main) solvent and the process contains a step of recycling unreacted solvent.

Preferably, the molar ratio of formaldehyde:ethylenediamine diacetic acid (or a salt thereof) is between 1.8:1 and 2.2:1. More than 2.2 molar equivalents of formaldehyde will give side reactions with phenol (which is also preferably dosed in a molar excess).

In yet another preferred embodiment it is ensured that the components, most importantly the EDDA, are fully dissolved in the reaction mixture during the process, which provides for a homogeneous reaction mixture that can be easily stirred and also leads to higher yields and less side products.

The invention is illustrated by the following Examples.

EXAMPLES

In all Examples where it is indicated that components are used in a certain percentage, like 95% phenol, the remaining percents are water. In addition, all solutions are aqueous solutions.

Example 1

Reaction of EDDA plus CH2O to phenol at a pH of about 5.5, using 0.96 eqv NaOH, 2 eqv CH2O, 12 eqv of phenol and a temperature of 35° C.

26.9 g of a 50% sodium hydroxide solution (0.336 mole) were added to a slurry of 62.3 g of 99% ethylenediamine-N,N'-diacetic acid (0.350 mole) in 131.3 g of water. 49.1 g of a 42.4% formaldehyde solution (0.693 mole) were added and the reaction mixture was stirred at room temperature for one hour to obtain a clear solution. This solution was added in one go to 444.7 g of 88.9% phenol (4.20 moles) and the container was washed with an additional 33.7 g of water. The reaction mixture was stirred at 35° C. for 24 h, during which time the pH increased from about 5 to close to 6. After 6 h, the o,o-HBED concentration was 10.85%, which corresponds to 59.7% yield. After 24 h, o,o-HBED was obtained in 83.1% yield according to HPLC (EN 13368-2: 2012).

Example 2

EDDA plus CH2O to phenol, pH about 6, using 0.97 eqv KOH, 2 eqv CH2O, 12 eqv phenol, 35° C.

45.6 g of a 44.7% potassium hydroxide solution (0.363 mole) were added to a slurry of 66.7 g of 99% ethylenediamine-N,N'-diacetic acid (0.375 mole) in 98.9 g of water. 52.0 g of a 43.6% formaldehyde solution (0.754 mole) were added and the reaction mixture was stirred at room temperature for 30 minutes to obtain a clear solution. This solution was added in 30 minutes to 447.7 g of 95% phenol (4.52 moles) and the reaction mixture was stirred at 35° C. for 24 h, during which time the pH increased from slightly below to slightly above 6. After 24 h, o,o-HBED was obtained in 83.1% yield according to HPLC (EN 13368-2: 2012).

Example 3

EDDA plus CH2O to phenol, pH about 6, using 0.98 eqv NaOH, 2 eqv CH2O, 12 eqv phenol, 25° C.

14.7 g of a 50% sodium hydroxide solution (0.184 mole) were added to a slurry of 33.4 g of 99% ethylenediamine-N,N'-diacetic acid (0.188 mole) in 49.6 g of water. 26.5 g of a 42.3% formaldehyde solution (0.373 mole) were added and the reaction mixture was stirred at room temperature for 30 minutes to obtain a clear solution. This solution was dosed in 30 minutes to 222.9 g of 95% phenol (2.25 moles) and the reaction mixture was stirred at 25° C. for 48 h, during which time the pH increased from about 5 to about 6. After 5 h, the o,o-HBED concentration was 8.11%, which corresponds to 38.7% yield. After 24 h, o,o-HBED was obtained in 73.6% yield according to HPLC (EN 13368-2: 2012). After 48 h, the o,o-HBED yield had increased to 79.6%.

Example 4

EDDA plus CH2O to phenol, pH about 6, using 0.98 eqv NaOH, 2 eqv CH2O, 12 eqv phenol, 45° C.

14.8 g of a 50% sodium hydroxide solution (0.185 mole) was added to a slurry of 33.5 g of 99% ethylenediamine-N,N'-diacetic acid (0.188 mole) in 49.8 g of water. 26.6 g of a 42.3% formaldehyde solution (0.375 mole) was added and the reaction mixture was stirred at room temperature for 30 minutes to obtain a clear solution. This solution was added in 30 minutes to 221.8 g of 95% phenol (2.24 moles) and the reaction mixture was stirred at 45° C. for 24 h, during which time the pH increased from about 5 to about 6. After 5 h, the o,o-HBED concentration was 15.36%, which corresponds to 72.8% yield. After 24 h, o,o-HBED was obtained in 76.8% yield according to HPLC (EN 13368-2:2012).

Example 5

EDDA plus CH2O to phenol, pH about 6, using 0.98 eqv NaOH, 2 eqv CH2O, 12 eqv phenol, 55° C.

14.6 g of a 50% sodium hydroxide solution (0.183 mole) were added to a slurry of 33.2 g of 99% ethylenediamine-N,N'-diacetic acid (0.187 mole) in 49.9 g of water. 26.5 g of a 42.3% formaldehyde solution (0.373 mole) were added and the reaction mixture was stirred at room temperature for 30 minutes to obtain a clear solution. This solution was added in 30 minutes to 222.2 g of 95% phenol (2.24 moles) and the reaction mixture was stirred at 55° C. for 24 h, during which time the pH increased from about 5 to about 6. After 5 h, the o,o-HBED concentration was 16.15% according to HPLC (EN 13368-2:2012), which corresponds to 77.6% yield. After 24 h, the o,o-HBED yield had slightly decreased.

Example 6

EDDA plus CH2O to phenol, pH about 6, using 0.98 eqv NaOH, 2 eqv CH2O, 6 eqv phenol, 35° C.

29.4 g of a 50% sodium hydroxide solution (0.368 mole) were added to a slurry of 66.9 g of 99% ethylenediamine-N,N'-diacetic acid (0.376 mole) in 110.9 g of water. 53.0 g of a 42.3% formaldehyde solution (0.747 mole) were added and the reaction mixture was stirred at room temperature for 30 minutes to obtain a clear solution. This solution was added in 30 minutes to 223.9 g of 95% phenol (2.26 moles) and the reaction mixture was stirred at 35° C. for 24 h, during which time the pH increased from about 5 to about 6 and the reaction product precipitated to give a slurry, which was a bit more difficult to handle than in the Examples where more phenol was used. After 24 h, o,o-HBED was obtained in 69.1% yield according to HPLC (EN 13368-2:2012).

Example 7

EDDA plus CH2O to phenol, pH about 5.5, using 0.98 eqv NaOH, 2 eqv CH2O, 16 eqv phenol, 35° C.

29.4 g of a 50% sodium hydroxide solution (0.368 mole) were added to a slurry of 66.8 g of 99% ethylenediamine-N,N'-diacetic acid (0.375 mole) in 109.1 g of water. 53.0 g of a 42.3% formaldehyde solution (0.747 mole) were added and the reaction mixture was stirred at room temperature for 30 minutes to obtain a clear solution. This solution was added in 30 minutes to 596.2 g of 95% phenol (6.02 moles) and the reaction mixture was stirred at 35° C. for 24 h, during which time the pH increased from about 5 to about 5.5. After 24 h, o,o-HBED was obtained in 82.7% yield according to HPLC (EN 13368-2:2012).

Example 8

CH2O plus phenol to EDDA, pH about 6 using 0.97 eqv NaOH, 2 eqv CH2O, 12 eqv phenol, 35° C.

50.5 g of a 44.4% formaldehyde solution (0.747 mole) were added to 445.9 g 95% phenol (4.50 moles). The pH decreased to 3.2. A slurry of 66.7 g of 99% ethylenediamine-N,N'-diacetic acid (0.375 mole) in 115.8 g water was added and the slurry was stirred for 15 minutes. During this time the pH decreased to about 3. 29.2 g of a 50% sodium hydroxide solution (0.365 mole) was added. Initially the pH increased to about 8, but after stirring for 30 minutes, the pH had decreased to about 6 and the reaction mixture had become homogeneous. The reaction mixture was stirred at 35° C. for 24 h, during which the pH increased somewhat again. After 24 h, o,o-HBED was obtained in 78.6% yield according to HPLC (EN 13368 2:2012).

Example 9

EDDA plus phenol to CH2O, pH about 6, using 0.97 eqv NaOH, 2 eqv CH2O, 12 eqv phenol, 35° C.

A slurry of 66.7 g of 99% ethylenediamine-N,N'-diacetic acid (0.375 mole) in 112.3 g of water was added to 445.7 g of 95% phenol (4.50 moles). 29.1 g of a 50% sodium hydroxide solution (0.364 mole) were added and the reaction mixture was stirred for 15 minutes at room temperature. During this period, the pH decreased from about 9 to about 8 as a result of dissolving part of the ethylenediamine-N,N'-diacetic acid. 51.6 g of a 43.6% formaldehyde solution (0.749 mole) were added to the slurry and after stirring for 10 minutes, during which time the pH decreased from 7.6 to 5.8, a clear solution was obtained. The reaction mixture was stirred at 35° C. for 24 h, during which time the pH increased from slightly below to slightly above 6. After 24 h, o,o-HBED was obtained in 81.5% yield according to HPLC (EN 13368-2:2012).

Example 10

EDDA plus phenol to CH2O, pH about 4, using 0.20 eqv NaOH, 2 eqv CH2O, 12 eqv phenol, 35° C.

66.8 g of 99% ethylenediamine-N,N'-diacetic acid (0.375 mole) were added to a mixture of 98.5 g of water and 446.1 g of 95% phenol (4.50 moles). 6.0 g of a 50% sodium hydroxide solution (0.075 mole) were added and the reaction mixture was stirred for 15 minutes at room temperature. During this period the pH decreased from about 8 to about 7 as a result of dissolving part of the ethylenediamine-N,N'-diacetic acid. 51.0 g of a 43.6% formaldehyde solution (0.740 mole) were added to the slurry and the pH decreased from about 7 to about 3. The reaction mixture was stirred at 35° C. for 24 h, during which time the pH increased from about 3 to about 4.5, and remained a slurry. After 24 h, o,o-HBED was obtained in 77.2% yield according to HPLC (EN 13368-2:2012).

Example 11

EDDA plus phenol to CH2O, pH about 5, using 0.60 eqv NaOH, 2 eqv CH2O, 12 eqv phenol, 35° C.

66.7 g of 99% ethylenediamine-N,N'-diacetic acid (0.375 mole) were added to a mixture of 103.1 g of water and 446.2 g of 95% phenol (4.50 moles). 18.1 g of a 50% sodium hydroxide solution (0.226 mole) were added and the reaction mixture was stirred for 15 minutes at room temperature. During this period the pH decreased from about 8.5 to about 8 as a result of dissolving part of the ethylenediamine-N, N'-diacetic acid. 51.2 g of a 43.6% formaldehyde solution (0.743 mole) were added to the slurry and the pH decreased from about 8 to about 4.5. The reaction mixture was stirred at 35° C. for 24 h, during which time the pH increased from about 4.5 to about 5.5 and remained a slurry. After 24 h, o,o-HBED was obtained in 80.3% yield according to HPLC (EN 13368-2:2012).

Example 12

EDDA plus CH2O to phenol, pH about 6, using 1.00 eqv NaOH, 2 eqv CH2O, 12 eqv phenol, 35° C.

30.0 g of a 50% sodium hydroxide solution (0.375 mole) were added to a slurry of 66.7 g of 99% ethylenediamine-N,N'-diacetic acid (0.375 mole) in 110.9 g of water. 50.1 g of a 44.6% formaldehyde solution (0.744 mole) were added and the reaction mixture was stirred at room temperature for 30 minutes to obtain a clear solution. This solution was added in 30 minutes to 446.9 g of 95% phenol (4.51 moles) and the reaction mixture was stirred at 35° C. for 24 h, during which time the pH increased from about 6 to 6.5. After 24 h, o,o-HBED was obtained in 79.5% yield according to HPLC (EN 13368-2:2012).

Example 13

EDDA plus CH2O to phenol, pH about 7.0, using 1.02 eqv NaOH, 2 eqv CH2O, 12 eqv phenol, 35° C.

30.7 g of a 50% sodium hydroxide solution (0.384 mole) were added to a slurry of 66.7 g of 99% ethylenediamine-N,N'-diacetic acid (0.375 mole) in 118.8 g of water. 50.1 g of a 44.6% formaldehyde solution (0.744 mole) were added and the reaction mixture was stirred at room temperature for 30 minutes to obtain a clear solution. This solution was added in 30 minutes to 449.2 g of 95% phenol (4.53 moles) and the reaction mixture was stirred at 35° C. for 24 h, during which time the pH decreased to about 7.0. After 24 h, o,o-HBED was obtained in 70.6% yield according to HPLC (EN 13368-2:2012).

Comparative Example 14

EDDA plus CH2O to phenol, pH about 8.0, using 1.10 eqv NaOH, 2 eqv CH2O, 12 eqv phenol, 35° C.

33.1 g of a 50% sodium hydroxide solution (0.414 mole) were added to a slurry of 66.8 g of 99% ethylenediamine-N,N'-diacetic acid (0.375 mole) in 114.9 g of water. 50.0 g of a 44.6% formaldehyde solution (0.743 mole) were added and the reaction mixture was stirred at room temperature for 30 minutes to obtain a clear solution. This solution was added in 30 minutes to 446.2 g of 95% phenol (4.50 moles) and the reaction mixture was stirred at 35° C. for 24 h, during which time the pH decreased to about 8. After 24 h, o,o-HBED was obtained in only 53.1% yield according to HPLC (EN 13368-2:2012).

Example 15

EDDA plus CH2O to phenol, pH about 6, using 0.98 eqv NaOH, 1.6 eqv CH2O, 12 eqv phenol, 35° C.

29.4 g of a 50% sodium hydroxide solution (0.368 mole) were added to a slurry of 66.8 g of 99% ethylenediamine-N,N'-diacetic acid (0.375 mole) in 111.5 g of water. 42.8 g of a 42.3% formaldehyde solution (0.603 mole) were added and the reaction mixture was stirred at room temperature for 30 minutes to obtain a clear solution. This solution was added in 30 minutes to 447.1 g of 95% phenol (4.51 moles) and the reaction mixture was stirred at 35° C. for 24 h, during which time the pH increased from about 5.5 to about 6. After 24 h, o,o-HBED was obtained in 55.6% yield according to HPLC (EN 13368-2:2012).

Example 16

EDDA plus CH2O to phenol, pH about 6, using 0.98 eqv NaOH, 1.8 eqv CH2O, 12 eqv phenol, 35° C.

29.4 g of a 50% sodium hydroxide solution (0.368 mole) were added to a slurry of 66.8 g of 99% ethylenediamine-N,N'-diacetic acid (0.375 mole) in 110.1 g of water. 48.1 g of a 42.3% formaldehyde solution (0.678 mole) were added and the reaction mixture was stirred at room temperature for 30 minutes to obtain a clear solution. This solution was added in 30 minutes to 445.9 g of 95% phenol (4.50 moles) and the reaction mixture was stirred at 35° C. for 24 h, during which time the pH increased from about 5.5 to about 6. After 24 h, o,o-HBED was obtained in 69.6% yield according to HPLC (EN 13368-2:2012).

Example 17

EDDA plus CH2O to phenol, pH about 6, using 0.97 eqv NaOH, 2.2 eqv CH2O, 12 eqv phenol, 35° C.

29.1 g of a 50% sodium hydroxide solution (0.364 mole) were added to a slurry of 66.7 g of 99% ethylenediamine-N,N'-diacetic acid (0.375 mole) in 108.9 g of water. 56.6 g of a 43.8% formaldehyde solution (0.826 mole) were added and the reaction mixture was stirred at room temperature for 30 minutes to obtain a clear solution. This solution was added in 30 minutes to 446.8 g of 95% phenol (4.51 moles) and the reaction mixture was stirred at 35° C. for 24 h, during which time the pH increased from about 5.5 to about 6. After 24 h, o,o-HBED was obtained in 85.2% yield according to HPLC (EN 13368-2:2012).

Comparative Example 18

PDDA plus CH2O to phenol, pH about 5, using 0.94 eqv NaOH, 2 eqv CH2O, 12 eqv phenol, 35° C.

7.9 g of a 49.2% sodium hydroxide solution (0.097 mole) were added to a slurry of 20.0 g of 98% propylenediamine-N,N'-diacetic acid (0.103 mole) in 46.5 g of water. 14.1 g of a 42.2% formaldehyde solution (0.198 mole) were added and the reaction mixture was stirred at room temperature for 30 minutes to obtain a clear solution with a pH of 6.8. This solution was added to 124.5 g of 90.4% phenol (1.20 moles). The pH was adjusted to about 5 with 1.4 g of 6M HCl and the reaction mixture was stirred at 35° C. No o,o-HBPD was formed after 24 hours according to HPLC. This Example demonstrates that the process of the present invention does not progress when using propylenediamine diacetic acid instead of ethylenediamine diacetic acid, though the chosen conditions (pH, temperature molar ratios) were all the same.

Comparative Example 19

(U.S. Pat. No. 2,967,196, Example 2 reworked with phenol instead of cresol). Reaction of EDDA and CH2O to phenol, pH about 10.5, using 2.0 eqv NaOH, 2 eqv CH2O, 2 eqv phenol, having methanol as a solvent, reflux 18.5 g of 95% ethylene-N,N'-diaminediacetic acid (0.100 mole) were dissolved in 12.7 g of water and 16.0 g of 50% sodium hydroxide solution (0.200 mole) to prepare a 46.6% aqueous solution of disodium ethylenediamine-N,N'-diacetate. The solution was mixed with 16.1 g of a 37.0% formaldehyde solution (0.198 mole) and 40 g of methanol. This homogeneous mixture was added dropwise over a period of 1 hour to a refluxing solution of 18.8 g of 99% phenol (0.198 mole) and 75.7 g of methanol. The resulting homogeneous mixture was allowed to react under reflux for an additional 8 hours and then cooled to room temperature. The pH of the reaction mixture was about 10.5. The o,o-HBED yield according to HPLC (EN 13368-2:2012) was 16% after 4 hours and 13% after 8 hours. This Example shows that a pH higher than 7 in combination with reflux conditions and low phenol content gives hardly any HBED product formation.

Comparative Example 20

(U.S. Pat. No. 2,967,196, Example 5 reworked with phenol instead of cresol). Reaction of EDDA and CH2O to phenol, using 1.2 eqv KOH, 2 eqv CH2O, 2 eqv phenol, having methanol as a solvent, reflux)

A heterogeneous mixture of 14.6 g 95% ethylenediamine-N,N'-diacetic acid (0.079 mole), 6.2 g 86.5% potassium hydroxide (0.096 mole), 5.2 g 90-92% paraformaldehyde (0.158 mole) and 158.8 g methanol was heated to reflux for 1 hour, until the mixture became homogeneous. The mixture was cooled and added dropwise over a period of 6 hours to a solution of 14.9 g 99% phenol (0.157 mole) and 34.3 g of methanol under reflux. The resulting homogeneous mixture was allowed to react under reflux for one additional hour and then cooled to room temperature. The o,o-HBED yield according to HPLC (EN 13368-2:2012) was 11%. This Comparative Example demonstrates that using little phenol and very high temperatures gives an extremely low yield. Also, it should be noted that more equivalents hydroxide were used than in Comparative Example 14, which will not help to produce a good yield either, as demonstrated above.

The invention claimed is:

1. Process to prepare N,N'-di(2-hydroxybenzyl) ethylenediamine-N,N'-diacetic acid (HBED) and salts thereof comprising a reaction between formaldehyde, ethylenediamine diacetic acid or a salt thereof (EDDA) and phenol at a pH of between 3 and 7 and a temperature below 60° C., wherein the reaction mixture contains 0.2 to 1.1 molar equivalents of alkali metal ions on the molar amount of EDDA.

2. Process of claim 1 comprising a first step wherein a reaction is performed between formaldehyde and ethylenediamine diacetic acid or a salt thereof to form an adduct, and a second step wherein the adduct of formaldehyde and ethylenediamine diacetic acid or a salt thereof is reacted with phenol while ensuring that the pH is between 3 and 7 and the temperature is below 60° C., wherein the reaction mixture contains 0.2 to 1.1 molar equivalents of alkali metal ions on the molar amount of EDDA.

3. Process of claim 1 comprising a first step of preparing a mixture comprising phenol and ethylenediamine diacetic acid or a salt thereof and a second step of reacting this mixture with formaldehyde at a pH of between 3 and 7 and a temperature of below 60° C., wherein the reaction mixture contains 0.2 to 1.1 molar equivalents of alkali metal ions on the molar amount of EDDA.

4. Process of claim 1 comprising a first step of preparing a mixture comprising phenol and formaldehyde and a second step of reacting this mixture with ethylenediamine diacetic acid or a salt thereof at a pH of between 3 and 7 and a temperature of below 60° C., wherein the reaction mixture contains 0.2 to 1.1 molar equivalents of alkali metal ions on the molar amount of EDDA.

5. Process of claim 1, wherein alkali metal ions are added to the reaction mixture by the addition of an alkali metal hydroxide or by adding the EDDA component as an ethylenediamine diacetate alkali metal salt or as an aqueous solution containing alkali metal ions.

6. Process of claim 1, wherein the pH is in the range from 4 to 7.

7. Process of claim 1, wherein the ethylenediamine diacetic acid or salt thereof is dissolved in the reaction mixture.

8. Process of claim 1, wherein the temperature is between 20 and 50° C.

9. Process of claim 1, wherein the molar ratio of phenol : EDDA is higher than 8:1.

10. Process of claim 9, wherein the molar ration of phenol: EDDA is between 10:1 and 14:1.

11. Process of claim 1, wherein the reaction is performed in phenol as a solvent.

12. Process of claim 1 containing an additional step of removing unreacted reactants or side products, a drying step, or both.

13. Process of claim 12, wherein the drying step is a spray drying step.

14. Process of claim 1 containing an additional step wherein the product is converted to the acid, another salt or metal complex.

* * * * *